(12) United States Patent
Dussaud et al.

(10) Patent No.: US 7,666,443 B2
(45) Date of Patent: Feb. 23, 2010

(54) DISPERSED PARTICLE COMPOSITIONS FOR ENHANCING POST WASH HYDRATION COMPRISING AMPHIPHILES AND MOISTURIZATION ADDITIVES OF DEFINED HLB

(75) Inventors: Anne Dussaud, Tarrytown, NY (US); Kavssery Parameswaran Ananthapadmanabhan, Woodbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 474 days.

(21) Appl. No.: 11/487,546

(22) Filed: Jul. 13, 2006

(65) Prior Publication Data

US 2008/0014168 A1    Jan. 17, 2008

(51) Int. Cl.
*A61K 8/02* (2006.01)
*A61P 17/16* (2006.01)
*A61Q 19/10* (2006.01)

(52) U.S. Cl. .............. 424/401; 514/873; 514/937; 514/975

(58) Field of Classification Search .............. None
See application file for complete search history.

(56) References Cited

U.S. PATENT DOCUMENTS

| 6,370,426 B1 | 4/2002 | Campbell et al. |
| 6,831,107 B2* | 12/2004 | Dederen et al. ............ 514/777 |
| 2005/0227907 A1* | 10/2005 | Lee et al. ................... 512/4 |

FOREIGN PATENT DOCUMENTS

| EP | 1 027 884 A1 | 8/2000 |
| EP | 1 433 476 A2 | 6/2004 |
| EP | 1 661 547 A1 | 3/2006 |
| WO | 00/33806 | 6/2000 |
| WO | 01/36952 A1 | 5/2001 |
| WO | 2005/030163 A1 | 4/2005 |

OTHER PUBLICATIONS

International Search Report Application No. PCT/EP2007/056381 mailed Feb. 7, 2008.
"Calibration of optothermal stratum corneum hydration measurements" Review of Scientific Instruments, AIP, Melville, NY, US, vol. 74, No. 1, 2003, pp. 729-731 XP 002435934.
Co-pending application: Dussaud et al. U.S. Appl. No. 11/487,533, filed Jul. 13, 2006 Method of Measuring and of Selecting Compositions of Enhanced Hydration Value.

* cited by examiner

*Primary Examiner*—Johann R Richter
*Assistant Examiner*—Frank I Choi
(74) *Attorney, Agent, or Firm*—Ronald A. Koatz

(57) ABSTRACT

The invention relates to compositions having enhanced post wash hydration by ensuring component or components of the composition meet selected defined criteria.

3 Claims, 4 Drawing Sheets

DISPERSED PARTICLE COMPOSITIONS FOR ENHANCING POST WASH HYDRATION COMPRISING AMPHIPHILES AND MOISTURIZATION ADDITIVES OF DEFINED HLB

FIELD OF THE INVENTION

The present invention relates to hydration of skin and/or hair. In particular it relates to compositions/systems to optimize and/or enhance hydration of skin and/or hair by ensuring that the applied compositions and components therein are maintained within defined parameters (i.e., relating to the hydrophilic-lipophilic balance, or HLB, of certain components and/or combination of components, and to the form the resulting compositions take). In a co-pending application, applicants disclose a method for determining enhanced hydration (to help define enhanced hydration compositions of the invention for example), as well as to methods for selecting compositions which will provide such enhanced hydration.

BACKGROUND

Enhanced hydration of skin and/or hair after application of formulations, in particular cleansing formulations, has multiple advantages. For example, hydration of skin (e.g., short term retention of water to the skin) can lead to consumer desirable cooling sensation as well as to a reduced tightness sensation. Enhanced hydration of the stratum corneum has additionally been shown to lead to softer skin for short periods after wash.

Typically, an enhanced hydration can be achieved in a variety of ways. For example, enhanced hydration values can be obtained through deposition of occlusive moisturizers (e.g., triglycerides, mineral oils). Such deposition may be accomplished, for example, using cationic polymers to enhance deposition of the moisturizers from the formulation; and/or the by direct transfer of structured oils (e.g., oils structured with a wax) such that the structured oils deposit more readily on skin.

Because of the tremendous consumer value of this moisturization effect, it would be very useful to understand what compositions and what compositional ingredients would provide such enhanced moisturization effect (i.e., hydration value).

Applicants have now found that when amphiphiles of specific HLB range are combined with specific moisturization additives of specific HLB range (such that combined amphiphile(s) and additive(s) are also within a specific HLB range) and with optional solvent, there will form specific particle size dispersions leading to enhanced post wash hydration. Failure to select components of specifically defined HLB range (and specifically defined combined HLB range) results in compositions which will not form the required dispersion and therefore not have the desired post wash hydration effect.

BRIEF DESCRIPTION OF THE INVENTION

In one embodiment (claimed in applicants co-pending application), applicants have found a method to measure exactly what part of the moisturization effect (e.g. hydration enhancement value) comes from additives used to provide said effect (e.g., occlusive moisturizers such as the triglycerides and mineral oils noted).

In this first embodiment, applications also disclose a method of selecting compositions providing post wash hydration effect which method involves measuring to determine the hydration enhancement value of the composition and selecting those compositions which have a measured value of at least a defined amount (e.g., value greater than about 27).

In a second embodiment, the subject of the present application, the invention relates to specific parameters (e.g., relating to HLB of specific compounds and specific combinations, as well as to the type of dispersion formed) which define the compositions of the invention having enhanced post-wash hydration.

More specifically, in one embodiment, the invention relates to a method of measuring the hydration value on skin which is attributable primarily to moisturizing additives (e.g., triglyceride, oil) wherein said method comprises:

(1) selecting at least one skin site to which a control composition without moisturizing additive (e.g., control cleansing system comprising surfactant or surfactants) will be applied and one skin site on the same skin surface to which a composition with moisturizing additive will be applied;

(2) prior to performing the wash protocol and applying control and non-control compositions, establishing a baseline skin hydration value through measurement of control $C_{c0}$ and non-control site $C_{nc0}$ or sites;

(3) applying said control composition and non-control composition to skin sites followed by rinsing and drying (typically the cleansing process takes about 2 to 6 minutes as described below, although this is not a criticality);

(4) recording multiple skin hydration values for a determined period of time (typically the process takes about 5 to 30 minutes as described below, although this is not a criticality);

(5) determining for each site a post-wash hydration value by subtracting a measured average baseline skin conductivity measured prior to wash on the same skin site from measured value of skin conductivity after the wash protocol or $(C_{ct}-C_{c0})$ and $(C_{nct}-C_{nc0})$;

(6) determining hydration enhancement value by calculating the mean change from baseline difference between the applied product and the control averaged across all subjects tested (1 or more) and all time points between about 5 to 20 mins (less than 5 minutes is fine as long as there are sufficient points to establish statistical significance). The HEV value for a given subject is:

$$HEV = \sum_{t=5\min}^{t=20\min} (C_{nct} - C_{nc0}) - (C_{ct} - C_{c0})$$

The HEV value is then averaged across the subjects.

This embodiment further provides a method of selecting enhanced hydration compositions by measuring the hydration value as set forth in steps (1)-(6), and then selecting compositions wherein the hydration enhancement value is greater than about 27. This is value above which hydration would be defined as "significant".

In a second embodiment, that of the subject invention, the invention relates to specific compositions or cleansing systems for enhancing post wash hydration. The compositions comprise (1) a surfactant system comprising one or more anionic or amphoteric amphiphiles having an HLB greater than about 20; (2) moisturization additive(s) having an HLB of between about 2 and 13, preferably 2 and 8; and (3) a solvent, wherein the concentrations of (1), (2) and (3) relative to one another form a "milky" dispersion (dispersion of particles varying in size between 0.05 and 1.0 micron) which remains stable (in same form) for at least 3 weeks at room temperature. The dispersed phase is formed by the moisturization additive(s).

Further, the surfactant(s) of (1) and moisturization additives of (2) have combined HLB of greater than 6 and less than 16, preferably between 8 and 14.

Preferably, the particle size of the moisturizing additive(s) dispersed in the surfactant phase is less than 1 micron, preferably between 0.1 and 0.4 microns.

While not wishing to be bound by theory, it is believed that conditions noted above allows the formation of a hydrophilic film and further allows that the dispersed moisturizing agent be deposited on the skin and/or hair. It is believed that, because of the hydrophilic moiety on the moisturization additive being deposited and forming a film, water can be retained for a longer time on the skin (hence the enhanced hydration value).

It is unexpected that a particular type of moisturizing agent (with specifically defined range of HLB), when used together with amphiphile(s) also within a defined HLB range, and together used to obtain a combined HLB within a specific range, would form a dispersion of the moisturizing additive of defined particle size in order to provide enhanced moisturization relative to formulated compositions which do not meet these parameters.

DETAILED DESCRIPTION OF THE INVENTION

Figure 1:
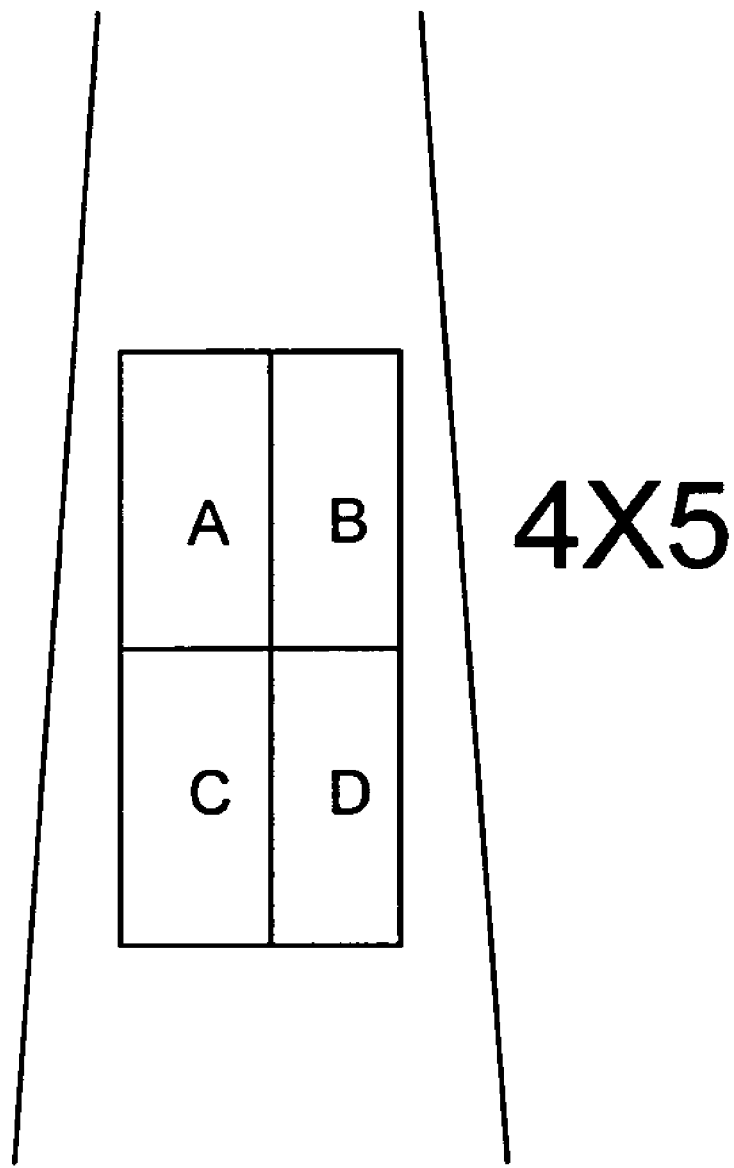
FIG. 1 is a schematic drawing of selected skin sites demarcated on a human forearm. A control or non-control composition are applied simultaneously on sites A and B. (Site A and B are separated, for example, by dental silicone impression rubber). Additional compositions and/or control can be applied to sites C and D on the same skin surface which are separately demarcated.
Figure 2:
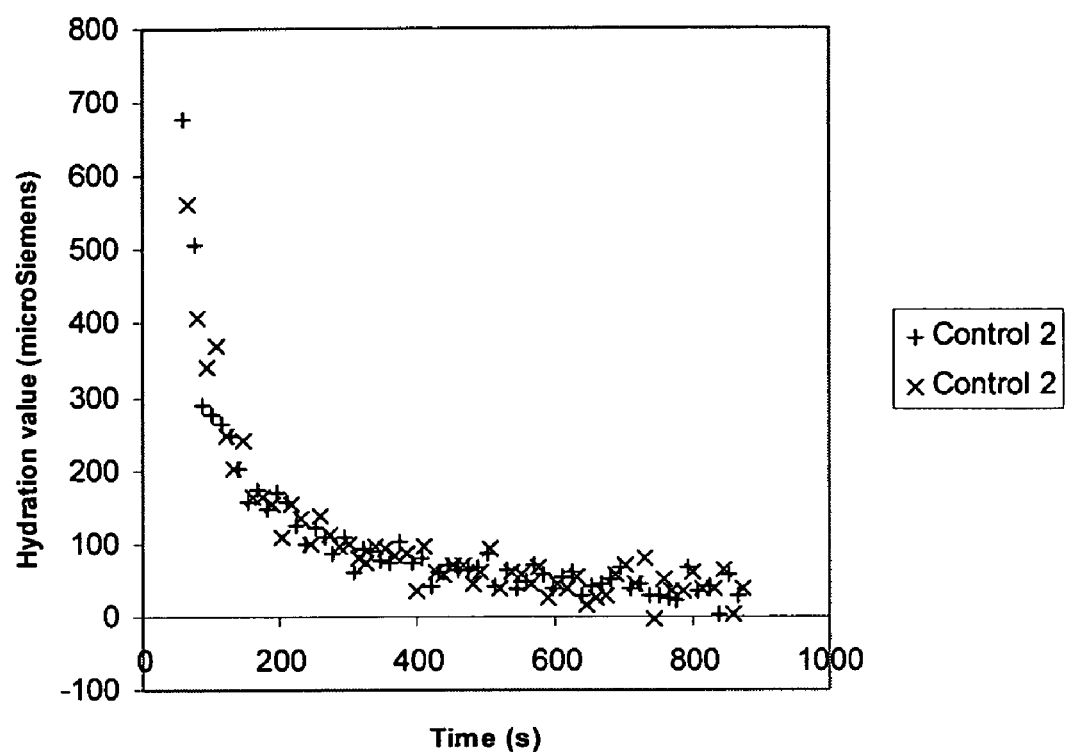
FIG. 2 is a graph representing absolute hydration values (on y-axis) for two identical control compositions measured over time (x-axis). The two control compositions are measured on the same arm and on sites next to one another. These two identical control bases are set forth as Control Example 2 and Control Example 2 in the examples. As indicated in the protocol, for each experiment there is a prior to wash and a post wash measurement, and the hydration value is calculated by subtracting pre-wash conductivity value from post wash conductivity value. As would be expected, there is little or no difference in the two control sites.

The invention relates to cleansing compositions providing enhanced post wash hydration or moisturization. According to the invention, specific amphiphiles (defined as molecules having both hydrophilic and hydrophobic groups, e.g., surfactants, emulsifiers) of defined HLB are mixed with moisturization additive or additives, also of specific HLB, to form compositions having a combined surfactant/additive HLB also of a defined range. The addition of additive forms a particle dispersion of the additive having a "milky" appearance when the additive(s) is mixed in. This particle dispersion is believed in turn responsible for the surprising moisturization effect when the specific parameters are met. In a copending application, applicants also claim a method of determining/measuring what the hydration value is (e.g., to see whether the value is enhanced or not), as well as a method of selecting compositions of enhanced hydration value based on measured values and defined levels of significance.

More particularly, hydrophilic-lipophilic balance (HLB) is based on the relative percentage of hydrophilic to hydrophobic groups in a surfactant molecule(s). Generally, surfactants of low HLB tend to form water-in-oil (W/O) emulsions, whereas those of high HLB form oil-in-water (O/W) emulsions.

A summary of HLB ranges typically required for various purposes is given by I. Becker in "Encyclopedia of Emulsion Technology", Marcel Bekker, Inc. (1983); Amphiphiles with HLB of about 3 to 6 are typically W/O emulsifier; amphiphiles of HLB about 7 to 9 are typically wetting agents; and amphiphiles with HLB about 8 to 18 are typically O/W emulsifier. Amphiphiles with HLB greater than 13 are typically detergents or solubilizers.

Davies (Proceedings of the Second International Congress on Surface Activity, Vol. 1 London, Butterworths, 1957, p. 440) has devised a method for calculating the HLB values for surfactants directly from their chemical formulas, introducing so-called group numbers, that is HLB numbers which correspond not to the molecule as a whole entity, but to the constituting groups (molecular structural units). Once the group numbers $g_i$ are known, one can calculate the HLB number from the chemical formula of a surfactant using the equation:

$$HLB = 7 + \sum_i g_i \qquad [1]$$

For hydrophilic groups, $g_i>0$; while for lipophilic groups, $g_i<0$. The letter "i" defines the number of groups.

In the case of a mixture of amphiphiles in water, the combined HLB is defined as follows:

$$HLB_c = \frac{\sum_j c_j HLB_j}{\sum_j c_j} \qquad [2]$$

where $c_j$ and $HLB_j$ are the weight concentration and the HLB value, calculated according to [1], of the amphiphile "j", respectively. All the HLB values are calculated at room temperature (about 25° C.).

It is well known that to increase the detergency of ionic surfactants or the lather stability, low HLB co-surfactants are used in conjunction with the HLB ionic surfactants. For example, typical low HLB co-surfactant are fatty acid, fatty alcohol or poly(oxyethylene)glycol alky ether. In that case, the mixing ratio of co-surfactant and ionic surfactant is chosen in order to form optimum mixed interfacial monolayer with lower surface tension. The low HLB amphiphile concentration is such that it forms co-micelles with the HLB surfactants and does not deposit readily on skin. By contrast, in the present invention it is believed that the low HLB amphiphile forms a dispersed phase, which deposits and has a head group which has strong affinity with water.

"Moisturization effect" refers to an increase of hydration of skin or hair with respect to a baseline value, which can be measured for example using conductivity.

In one embodiment, the invention relates to a method of measuring what amount of moisture retention is attributable to an additive used to provide moisturization (e.g., in reality any given compositional element which can provide moisture) to the skin. The method factors out other values which are present and affect or provide moisturization (evaporation, environmental conditions) to focus on that amount attributable to the component. Using such method, it is possible to determine what precisely are the optimal moisturizer additives which can be used.

This method comprises:

(1) selecting one or more skin sites to which a control composition without the tested component (e.g., moisturizer) is applied (such control composition is preferably a cleansing composition which will comprise one or more surfactants); and one or more skin sites on the same skin surface to which the control composition plus the tested component will be applied;

(2) prior to performing wash protocol and applying the control and non-control compositions of (1), establishing a baseline skin hydration value on the site(s) to which the control and non-control compositions will be applied through measurement of control $C_{co}$ and non-control $C_{nco}$ site or sites.

(3) applying the control and non-control compositions to the respective skin sites followed by rinsing and drying;

(4) recording multiple skin hydration values on the site or sites on which the control and non-control compositions have been applied for a determined period of time (typically application process will take about 2-6 minutes as described in protocol and below, although this is not a criticality);

(5) determining for each site a post-wash hydration value by subtracting a measured average baseline skin conductivity measured prior to wash ($C_o$ or $C_{nco}$) on the same skin site from the measured value of skin conductivity after the wash protocol ($C_{ct}$ or $C_{nct}$) measured as ($C_{ct}-C_{co}$) and ($C_{nct}-C_{nco}$), where $C_{ct}$ and $C_{nct}$ are measured conductivities at given time; and (6) determining a hydration enhancement value (HEV) by calculating the mean change from baseline difference between the applied product and the control product averaged across all subjects tested (1 or more) and all time points between 5 and 20 minutes. The HEV value for a given subject is:

$$HEV = \sum_{t=5\min}^{t=20\min} (C_{nct} - C_{nco}) - (C_{ct} - C_{co}),$$

The HEV value is then averaged across all subjects.

It is noted that 5 and 20 minutes are not criticalities. The lower limit, for example, is simply what is enough to have statistical meaning. In theory there is no upper limit.

This embodiment of the invention further comprises a method for selecting a composition having enhanced post wash hydration which comprises measuring the HEV according to steps (1)-(6) noted above, and selecting those compositions having a defined "significant" value for hydration enhancement. While applicants have defined on HEV value of greater than about 27 as significant, it should be understood that any value might in theory be considered significant depending on what is considered "sufficient" hydration for the defined audience. Thus, hydration values greater than about 15 (e.g., control with no additive has HEV of 15), preferably greater than about 20 and more preferably greater than about 27 might be used.

The selected skin site for testing is typically an area on the arm such as the forearm, although in theory it can be applied to any skin. The control and non-control sites should ideally be in the same proximate area in order to ensure minimal if any variation in testing. If two areas tested are immediately adjacent to one another (see FIG. 1), the testing area is delimited with a barrier such as, for example, dental rubber. This barrier prevents cross contamination of the sites.

The base line value (before applying control or non-control) is established by multiple readings (only one is needed although typically, about 10 to 20 values are taken) of the skin hydration in the tested area. The hydration value can be measured, for example, using electrical capacitance and conductance of the skin as indicators of the hydration. These in turn can be measured using equipment such as Skicone® 200 hygrometers. Other equipment to measure hydration may include Corneometer® CM420 hydrometer and Servo Med EPI® evaporimeters. Besides conventional corneometry, additional methods for measuring hydration may include nuclear magnetic resonance spectroscopy (NMR-5) and transient thermal transfer (TTT). In any event, methods for obtaining hydration values are well known and well understood by those skilled in the art.

After obtaining baseline measurements, control compositions and non-control compositions are applied to selected measured area and standard wash protocol are applied.

The compositions preferably are surfactant containing compositions (containing at least one surfactant) although, the method can be used for any composition. Typically tested compositions comprised a blend of anionic and/or nonionic surfactants and water.

After rinsing and drying (typically although not necessarily by drying with paper towel), skin hydration values are then recorded as a function of time (e.g., 1 reading/second for a period of time basically 15 minutes to an hour).

Post wash hydration values are then obtained by substracting a measured average basis on conductivity (or whatever value used) prior to wash from the measured value after rinse and drying.

Final values of enhanced hydration are obtained by calculating mean change from baseline difference between the applied product and the control product averaged across all subject (including all areas on each subject and all time points.

A typical measurement is as follows:

(1) 2 ml of cleansing system (control and non-control) are applied to wet cloths. A clinician typically will produce lather with each sample for a few seconds;

(2) the appropriate test site (control and non-control) is moistened with gentle flow of warm water (about 40° C.) for specified time (typically 15-60 seconds);

(3) the test sites are washed by a clinician at the same time for a specified time (typically 5-30 seconds);

(4) products are left on the site for specified time (typically 60-120 seconds);

(5) the test sites are rinsed for $\geq 15$ seconds and typically patted dry; care should be taken not to run onto other sites.

Results are then recorded as per steps (4)-(6) of the method noted earlier.

In a second embodiment, the subject of the present invention, the invention relates to a specific composition or cleansing system for enhancing post hydration. The compositions comprise:

(1) a surfactant system comprising one or more anionic or amphoteric amphiphiles having HLB greater than about 20;
(2) moisturization additives having an HLB between about 2 and 13, preferably 2 and 8; and
(3) a solvent;
wherein weight concentrates of (1), (2) and (3) allow formation of a milky dispersion;
wherein the dispersed phase is formed by addition of the moisturization additive(s).

In addition, the amphiphile mix (1) and additive(s) of (2) have combined HLB greater than 6 and less than 16, preferably between 8 and 14. By "milky dispersion is meant a dispersion of particles of size 0.05 to 1.0, preferably 0.1 and 0.4 microns, and which form spontaneously under mixing conditions. For the dispersion, the particles do not coalesce, flocculate or agglomerate over some period of time (e.g., at least 2 weeks) due to thermal agitation (e.g., Brownian motion).

While not wishing to be bound by theory, the noted conditions appear to allow formation of a hydrophobic film while, because of the hydrophilic moiety of the low HLB additive, water can be retained.

Suitable anionic or amphoteric amphophiles of (1) with HLB>20 are disclosed, for example, in Laughlin, R. G., "The Aqueous Phase Behavior of Surfactants", Academic Press, New York (1994). Non-limiting examples of suitable high HLB amphiphiles include anionics such as alkyl sulfates (including acyl isethionates), alkyl ether sulfates, alkyl sulfonates, alkyl carboxylates, alkyl ether carboxylates, alkyl aminocarboxylates, taurates, sulfosuccinates, sarcosinates and monoalkyl phosphates.

It should be noted that HLB of surfactants with pH dependent functional groups (e.g., carboxylates which may be in form of soap or fatty acid; glycinates—glycinic acid; phosphates, phosphoric acid, etc.) is in fact dependent on pH since there will be a combination of anionic species and uncharged species at intermediate pH values. For such surfactants, the effective HLB will correspond to the mixture of corresponding acids and anionic species.

Typical co-surfactants which can be used include fatty acids or long chain alcohols.

The moisturizing additive 2 should have an HLB value between 2 and 13 and preferably have a hydrophilic head group forming multiple hydrogen bonds with water. Typical water-in-oil emulsifier include fatty acid esters of sugar derivatives (fatty acid esters of anhydrosorbitols, fatty acid esters of glycerol). Other examples are and also alkoxylated triglyceride oils. Other examples include water/oil emulsifiers such as cetylpolyethyleneglycol/polypropyleneglycol dimethicone.

The solvent is a polar solvent, including water, polyols and may contain other ingredients such as buffers and/or stabilizers. Preferably the weight concentration is greater than 50%, more preferably greater than 70%.

EXAMPLES

Protocol

Control and non-control compositions are applied as described above. Typically, 2 milliliters of system is applied to cloth and a clinician produces lather for a few seconds. The test site(s) are than moistened with warm water (about 40° C.) for specified time (5 to 60 seconds). Test site(s) are washed for about 5 to 30 seconds and product remains on the site (for 60 to 120 seconds). The test site is than rinsed and dried.

Skin hydration values are recorded and a post wash hydration value is determined by subtracting measured average baseline skin conductivity measured prior to wash, from measured value of conductivity after the wash. Hydration enhancement values can than be calculated.

Examples 1-18

The Examples below set forth various compositions which are prepared and applied to skin according to the invention. In each case, the final compositions (shown) were measured and compared to composition without moisturizing additive.

Figure 3:
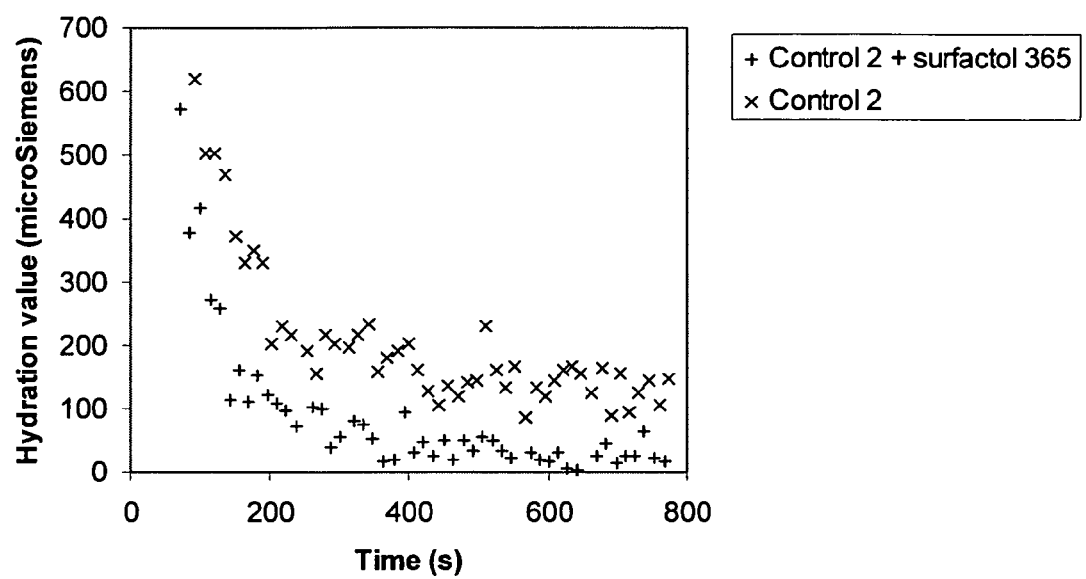
FIG. 3 is graph of absolute hydration value for two compositions wherein one (marked by "x") is a control (similar to FIG. 2) and the other site is the same control with Surfactol® 365 (PEG-40 castor oil) added to the control (marked by "+").

As can be seen from results summarized in Table 1 after all the examples and from FIG. 3, when the HLB is within defined ranges, optimal hydration values (e.g., >27) are obtained.

Figure 4:
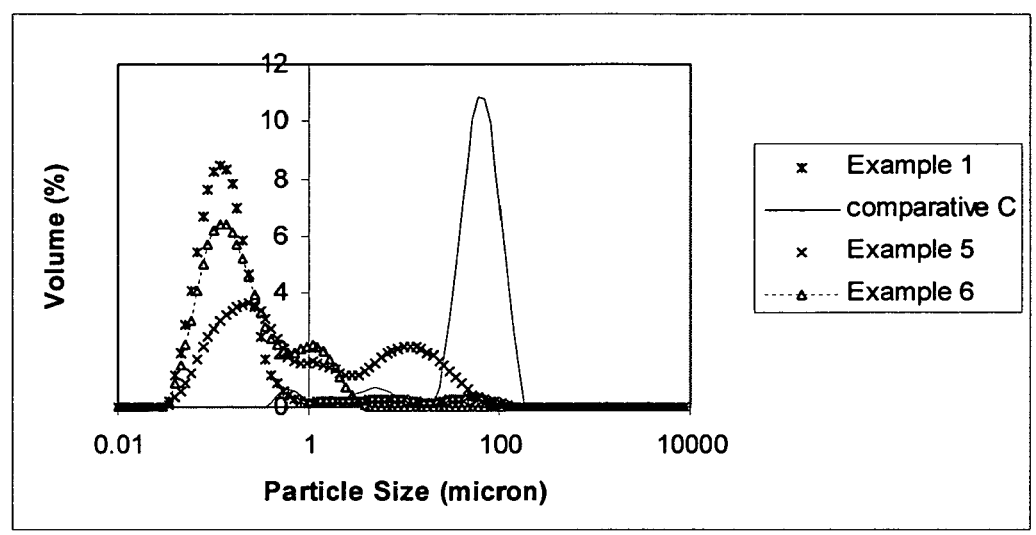
FIG. 4 is a graph of particle size distribution of various examples of the invention (and a Comparative). This figure and separate Table of median of particle distribution (Table 2 discussed in examples) show that milky dispersions of invention (with optional hydration) have droplet size of dispersed moisturizing oil less than 1 micron whereas comparative (not displaying enhanced hydration) is a dispersion with much larger particles.

Effect of enhanced hydration based on particle size can be seen from Table 2 and FIG. 4. Specifically, FIG. 4 displays the particle size distribution measured with the Mastersizer Malvern 2000 for Examples 1, 5, 6 and Comparative C. For particle characterization with the Mastersizer, the sample was diluted with the surfactant phase without the moisturizing additive size (control). The ratio of the sample to the dispersing phase (control) was adjusted in order to reach a laser obscuration between 10-20%. The stirrer pump speed was 2975 rpm. The refractive index of the moisturizing oils and the surfactant were measured with an Abbe Mark II Reichert refractometer. The average displayed in FIG. 4 and Table II are averaged of 20 measurements, which were obtained by 10,000 readings. Table II shows the median of the particle distribution d(0.5) for the same examples. The median of the particle size distribution is the size above which we can find 50% of the volume of all the particles. The plot and Table II show that the milky dispersions leading to optimal hydration values have droplet size of the dispersed moisturizing oil which is less than 1 micron, whereas Comparative C which is not displaying enhanced hydration is a dispersion with much bigger particles. It should also be noted that the Comparative Examples D-I, which are not displaying enhanced hydration, are clear solutions and have micellar particles too small to be detected by the Mastersizer.

| Component | Example 1 | | | |
|---|---|---|---|---|
| | Amphiphile HLB | % by wt. | Combined HLB of composition* | Enhanced Hydration Value |
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| PEG-5 castor oil (Additive) | 3.6 | 5% | | |
| Water | | 80% | | |
| | | | 12.92 | 30.4 |

*For this and other composition examples, this refers to combined HLB of surfactant(s) and of moisturization additive or additives.

Example 2

| Component | Amphiphile HLB | % by wt. | Combined HLB of composition | Enhanced Hydration Value |
|---|---|---|---|---|
| Potassium cocoyl glycinate | 23.1 | 4/5% | | |
| Cocoyl glycinic acid | 4 | 4.5% | | |
| Sodium lauryl amphoacetate | 25 | 4.5% | | |
| Lauric acid | 4 | 1.5% | | |
| PEG-40 castor oil (Additive) | 13.3 | 5% | | |
| Water | | 80% | | |
| | | | 15.35 | 31.2 |

Example 3

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| PEG-5 castor oil (Additive) | 3.6 | 10% | | |
| Water | | 80% | | |
| | | | 11 | 69 |

Example 4

| Component | Amphiphile HLB | % by wt. | HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| PEG-40 castor oil (Additive) | 13.3 | 10% | | |
| Water | | 80% | | |
| | | | 15 | 69 |

Example 5

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| Sorbitan stearate (Additive) | 5 | 5% | | |
| Water | | 80% | | |
| | | | 13 | 84 |

Example 6

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| Glyceryl oleate (Additive) | 3 | 5% | | |
| Water | | 80% | | |
| | | | 13 | 39.4 |

Example 7

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| PEG-7 glyceryl cocoate (Additive) | 11 | 5% | | |
| Water | | 80% | | |
| | | | 15 | 37 |

Comparative A

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| PEG-20 glyceryl oleate (Additive) | 15 | 5% | | |
| Water | | 80% | | |
| | | | 16 | 5 |

Comparative B

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinic acid | 4 | 4.5% | | |
| Sodium lauryl amphoacetate | 25 | 4.5% | | |
| Lauric acid | 4 | 1.5% | | |
| PEG-20 glyceryl laurate (Additive) | 16 | 5% | | |
| Water | | 80% | | |
| | | | 16 | −16 |

Comparative C

| Component | Amphiphile HLB | % by wt. | Combined HLB of composition | Enhanced Hydration Value |
|---|---|---|---|---|
| Cocamido-sulfosuccinate | 44 | 9% | | |
| Sodium lauryl amphoacetate | 25 | 4.5% | | |
| Lauric acid | 4 | 1.5% | | |
| PEG-5 castor oil (Additive) | 3.6 | 5% | | |
| Water | | 80% | | |
| | | | 22 | −19 |

Comparative D

| Component | Amphiphile HLB | % by wt. | Combined HLB of composition | Enhanced Hydration Value |
|---|---|---|---|---|
| Betaine | 21.1 | 10% | | |
| SLES | 41 | 5% | | |
| PEG-5 castor oil (Additive) | 3.6 | 5% | | |
| Water | | 80% | | |
| | | | 22 | −21 |

Comparative E

| Component | Amphiphile HLB | % by wt. | Combined HLB of composition | Enhanced Hydration Value |
|---|---|---|---|---|
| Betaine | 10 | 9% | | |
| SLES | 5 | 4.5% | | |
| PEG-5 castor oil (Additive) | 3.6 | 10% | | |
| Water | | 80% | | |
| | | | 23 | 26 |

Comparative F

| Component | Amphiphile HLB | % by wt. | Combined HLB of composition | Enhanced Hydration Value |
|---|---|---|---|---|
| SLES | 41 | 15% | | |
| PEG-5 castor oil (Additive) | 3.6 | 10% | | |
| Water | | 75% | | |
| | | | 26 | 1 |

Comparative G

| Component | Amphiphile HLB | % by wt. | Combined HLB of composition | Enhanced Hydration Value |
|---|---|---|---|---|
| SLES | 41 | 15% | | |
| PEG-5 castor oil (Additive) | 3.5 | 20% | | |
| Water | | 65% | | |
| | | | 20 | 0 |

Comparative H

| Component | Amphiphile HLB | % by wt. | Combined HLB of composition | Enhanced Hydration Value |
|---|---|---|---|---|
| SLES | 41 | 15% | | |
| PEG-40 castor oil (Additive) | 13.3 | 20% | | |
| Water | | 65% | | |
| | | | 25 | −8 |

Comparative I (Control)

| Component | Amphiphile HLB | % by wt. | Combined HLB of composition | Enhanced Hydration Value |
|---|---|---|---|---|
| Potassium cocoyl glycinate | 23.1 | 4.5% | | |
| Cocoyl glycinate | 4 | 4.5% | | |
| Sodium lauryl amphoacetate | 25 | 4.5% | | |
| Lauric acid | 4 | 1.5% | | |
| Water | | 85% | | |
| | | | 16 | 15 |

TABLE 1

Summary Table

| | Additive | Surfactant Base | Combined HLB | Hydration Value | Dispersion Appearance |
|---|---|---|---|---|---|
| Example 1 | Peg-5 castor oil 5% | glycinate | 13 | 30 | Milky |
| Example 2 | Peg-40 castor oil 5% | glycinate | 15 | 31 | Milky |
| Example 3 | Peg-5 castor oil 10% | glycinate | 11 | 69 | Milky |
| Example 4 | Peg-40 castor oil 10% | glycinate | 15 | 69 | Milky |
| Example 5 | Sorbitan stearate 5% | glycinate | 13 | 84 | Milky |
| Example 6 | Glyceryl oleate 5% | glycinate | 13 | 39 | Milky |
| Example 7 | Peg-7 glyceryl cocoate 5% | glycinate | 15 | 37 | Milky |
| Comparative A | Peg-20 glyceryl oleate 5% | glycinate | 16 | 5 | N/A |
| Comparative B | Peg-20 glyceryl laurate 5% | glycinate | 16 | −16 | N/A |
| Comparative C | Peg-5 castor oil 5% | Sulfosuccinate | 22 | −19 | White |
| Comparative D | Peg-5 castor oil 5% | SLES/betaine | 22 | −20.5 | Clear |
| Comparative E | Peg-5 castor oil 10% | SLES/betaine | 23 | 26 | Clear |
| Comparative F | Peg-5 castor oil 10% | SLES | 20 | 1.4 | Clear |
| Comparative G | Peg-5 castor oil 20% | SLES | 26 | 0.2 | Clear |
| Comparative H | Peg-5 castor oil 20% | SLES | 25 | −7.8 | Clear |
| Comparative I (Control) | None | glycinate | 16 | 15 | Clear |

TABLE 2

| Example | D[0.5] (microns) |
|---|---|
| Example 1 | 0.146 |
| Example 5 | 0.638 |
| Example 6 | 0.192 |
| Comparative C | 64.221 |

The invention claimed is:

1. Composition for enhancing post wash hydration comprising:
   (1) surfactant system comprising a combination of anionic surfactant having HLB>20 and amphoteric amphiphile having HLB >20, wherein the anionic surfactant is an alkyl glycinate and the amphoteric amphiphile is an alkyl amphoacetate;
   (2) a moisturization additive having HLB greater than 2 and less than 13 selected from the group consisting of fatty acid esters of sugar derivatives; alkoxylated triglyceride oils; alkyl dimethicone and mixtures thereof; and
   (3) solvent,
   wherein the concentration of surfactant(s) and of additive or additives of (2) is such that combined HLB is greater than 6 and less than 16;
   wherein said additive(s) form a particle dispersion with particles ranging in size from 0.05 to 1.0 micron
   wherein, after applying particle dispersion compositions to skin, there are obtained hydration values >27.

2. A composition according to claim 1, wherein additive (2) dispersed in a surfactant phase formed from the surfactant or surfactants has size of 0.1 to 0.4 microns.

3. A composition according to claim 1, wherein said moisturization additive is fatty acid ester of sorbitan or glycerol.

* * * * *